US008998835B2

(12) United States Patent
McVicker

(10) Patent No.: US 8,998,835 B2
(45) Date of Patent: Apr. 7, 2015

(54) METHOD OF USING A COMPRESSION BANDAGE

(75) Inventor: Nola Janene McVicker, Energy, IL (US)

(73) Assignee: Sun Glitz Corporation, Energy, IL (US)

( * ) Notice: Subject to any disclaimer, the term of this patent is extended or adjusted under 35 U.S.C. 154(b) by 905 days.

(21) Appl. No.: 11/837,086

(22) Filed: Aug. 10, 2007

(65) Prior Publication Data

US 2008/0045876 A1 Feb. 21, 2008

Related U.S. Application Data

(60) Provisional application No. 60/822,743, filed on Aug. 17, 2006.

(51) Int. Cl.
*A61L 15/00* (2006.01)
*A61F 13/02* (2006.01)

(52) U.S. Cl.
CPC .................................. *A61F 13/0273* (2013.01)

(58) Field of Classification Search
USPC ........................................................... 602/75
See application file for complete search history.

(56) References Cited

U.S. PATENT DOCUMENTS 4,005,709 A 2/1977 Laerdal
4,377,160 A * 3/1983 Romaine ........................... 602/2
4,424,808 A 1/1984 Schafer et al.
4,484,574 A * 11/1984 DeRusha et al. ................ 602/75
4,661,099 A 4/1987 von Bittera et al.
4,699,133 A 10/1987 Schafer et al.
4,806,404 A * 2/1989 Cascino ....................... 428/40.4
4,838,253 A 6/1989 Brassington et al.
5,006,401 A 4/1991 Frank
5,156,589 A 10/1992 Langen et al.
5,230,701 A 7/1993 Meyer et al.
5,939,339 A * 8/1999 Delmore et al. .............. 442/149
RE36,459 E * 12/1999 McVicker ..................... 428/222
6,048,326 A 4/2000 Davis et al.
6,194,629 B1 2/2001 Bernhard
6,254,554 B1 * 7/2001 Turtzo ........................... 601/134
6,296,618 B1 * 10/2001 Gaber ............................. 602/75
6,296,918 B1 * 10/2001 Choi et al. ...................... 428/77
6,338,723 B1 * 1/2002 Carpenter et al. .............. 602/75
6,375,639 B1 4/2002 Duplessie et al.
6,528,697 B1 3/2003 Knutson et al.
6,533,746 B1 * 3/2003 Ritchie ........................... 602/75
6,555,730 B1 4/2003 Albrod et al.
6,573,419 B2 6/2003 Naimer
6,575,926 B2 * 6/2003 Bonutti ........................... 602/75
6,593,508 B1 7/2003 Harder
6,663,584 B2 12/2003 Griesbach, III et al.
6,759,566 B1 7/2004 Court et al.
6,762,338 B2 7/2004 Harder
6,811,540 B1 * 11/2004 Ritchie ........................... 602/26
6,852,089 B2 * 2/2005 Kloecker et al. ................ 602/75

(Continued)

OTHER PUBLICATIONS

"Compression Garments", Coban Ace, examples of Compression Garments, 1 page.

(Continued)

*Primary Examiner* — Victoria J Hicks
(74) *Attorney, Agent, or Firm* — Barnes & Thornburg LLP

(57) ABSTRACT

A compression dressing and method of use is provided. The dressing is self-adherent, washable and reusable and provides a selected and generally constant pressure to the surface of an animal.

22 Claims, 2 Drawing Sheets

10
14
12

(56) References Cited

U.S. PATENT DOCUMENTS

| | | | | |
|---|---|---|---|---|
| 6,869,410 | B1 * | 3/2005 | Mosemiller | 602/1 |
| 6,974,428 | B2 | 12/2005 | Knutson et al. | |
| 6,981,506 | B2 | 1/2006 | Court et al. | |
| 6,998,510 | B2 | 2/2006 | Buckman et al. | |
| 7,022,111 | B2 | 4/2006 | Duplessie et al. | |
| 7,135,007 | B2 * | 11/2006 | Scott et al. | 602/75 |
| 7,264,605 | B2 * | 9/2007 | Gaylord | 602/26 |
| 2002/0052570 | A1 | 5/2002 | Naimer | |
| 2003/0036715 | A1 | 2/2003 | Knutson et al. | |
| 2003/0036716 | A1 | 2/2003 | Knutson et al. | |
| 2003/0040691 | A1 | 2/2003 | Griesbach, III et al. | |
| 2003/0176828 | A1 | 9/2003 | Buckman et al. | |
| 2004/0097855 | A1 | 5/2004 | Page et al. | |
| 2004/0153040 | A1 | 8/2004 | Martineau et al. | |
| 2004/0199096 | A1 | 10/2004 | Court et al. | |

OTHER PUBLICATIONS

Anonymous Article on Foam Tech website entitled “What is the Difference Between Open-cell and Closed-cell Polyurethane Foams”, 1 page, http://www.foam-tech.com/products/urethane__foam/open__closed__cell.htm, Copyright 2008 Building Envelope Solutions, Inc.

* cited by examiner

METHOD OF USING A COMPRESSION BANDAGE

This application claims priority to and the benefit of U.S. Provisional Patent Application Ser. No. 60/822,743 filed Aug. 17, 2006, the disclosure of which is now incorporated herein by reference.

FIELD OF THE INVENTION

The present invention relates generally to compression wrappings, and more specifically to self-adherent compression wrap formed of elongated strips of foamed plastic.

BACKGROUND OF THE INVENTION

The current state of the art in various medical procedures, such as for example cosmetic surgery, is to wrap a surgery site with bandages to provide compression to the surgery site. Bandages have also been used to wrap animal body parts to provide support, such as in the case of a broken or sprained limb or joint. For example, commonly owned U.S. Pat. No. Re. 36,459, the disclosure of which is incorporated herein by reference, discloses a foam wrapping for providing support. As discussed at column 1 of the '459 patent, the wrapping material is formed of elongated strips of vinyl foam which has had excess plasticizer cast into its mixture which allows the foam to adhere to itself and most surfaces. In contrast to and distinct from providing support, which lifts and aids the animal in bearing weight on the injured limb or joint, a compression wrap tends to apply a pressure to an area in order to generally diminish its volume and augment its density. Therefore, compression wraps, rather than providing support or weight bearing assistance, which illustratively requires tighter wrapping, tend to decrease swelling, promote tissue adherence, provide comfort and relieve suture tension. Compression wraps may be used for post-operative recovery after such procedures as for example and without limitation liposuction, breast augmentation, breast lifts, breast reductions, face lifts, facial implants, neck lifts, tummy tucks, varicose vein procedures, burn therapy and the like.

Representative bandages or wrappings used in compression wrapping include for example Ace and Coban bandages, as well as self-adherent flexible bandages that have an impregnation of adhesive into a cloth membrane which allows the wrapping to stick to itself. One problem with these wrappings is that the material tends to expand, slip and/or stretch out of shape, thereby failing to keep the compression steady where needed or to the degree that is needed to optimize the post-operative recovery. Also, the inability to easily remove, reapply and/or wash such wrappings limits their life span.

It is also possible to use a "garment" such as for example a girdle or facial brassieres or bands, alone or in combination with the above mentioned wrappings or bandages. These garments are typically pre-fabricated rather than being fitted specifically for each patient. Therefore, they are either too difficult to put on and/or take off, or they slip on and off too easily. In addition, they may alternately be overly restrictive, uncomfortable and/or unable to provide sufficient compression. Also, cutting them to fit a particular individual may not be optimal and may even destroy the garment.

What is needed is a self-adherent and flexible wrap or bandage that provides compression where needed, when needed, and as needed. Such a bandage illustratively would exert a light, steady pressure on the wrapped area, yet stay in place, would be easily removed and reapplied, and would be washable and reusable. Illustratively, such a bandage could but need not be padded and would conform to the patient's shape or body contour. Also, the compression bandage could accommodate an optional dressing separate from and underlying the bandage. Compression wraps illustratively may need to be worn for extended periods, making comfort and shape/position retention desirable.

One illustrative example of a suitable wrapping material of this invention utilizes technology which is the base subject of U.S. Pat. No. 4,806,404, which is incorporated herein by reference. The wrapping material illustratively is formed of elongated strips of a vinyl foam which has had excess plasticizer cast into its mixture which allows the foam to adhere to itself and most surfaces. As discussed at column 2 lines 2-12 of the '404 patent, the foam material may be a foamable polymer material such as foamable polyvinyl chloride, foamable polyurethane, or the like. An excess amount of a plasticizer such as a phthalate based compound is added to the polymeric base material to allow layer 16 to demonstrate high tack qualities. Preferably, the plasticizer accounts for at least 40% of tack layer 16 by weight but lower plasticizer concentrations may be sufficient in some applications depending upon the plasticizer and foamable resins used. Other compounds may be added to the mixture for stabilizing purposes. Illustratively, the wrap can be washed and reused since the plasticizer is incorporated directly into the final product as opposed to being added as a surface adhesive. The foam would provide comfort for the patient. Illustratively, the wrap may, but need not have release or backing paper.

SUMMARY OF THE INVENTION

The present invention may comprise one or more of the following features and combinations thereof.

A compression dressing and method of use are provided. The compression dressing illustratively may comprise strip means. The strip means illustratively may comprise elongated strips. The strips may also form a compression dressing, and illustratively may be a bandage. The strips illustratively may be self-adherent and may comprise a foamed material. The foamed material illustratively may include a polymer. Illustratively, about 40 weight percent of the foamed material is a plasticizer. It may be desirable that at least 40 weight percent of the foamed material is a plasticizer. A user may illustratively apply the strips, bandage or dressing to the surface in a spiral wound overlap fashion, without the use of a separate adhesive, so that the strip means, strip, or bandage contacts and adheres to itself and the surface to form the compression dressing in contact with the surface of an animal. The animal may be a human or any other mammal, reptile, fish, bird and the like. The strip or bandage may apply and maintain a selected pressure to the surface and may conform to the contour of the surface. The user may vary the pressure and contour of the dressing, strip or bandage as desired and may remove, wash and reapply in any desired way.

These and other aspects of the present invention will become more apparent from the following description of the illustrative embodiment.

DESCRIPTION OF THE ILLUSTRATIVE EMBODIMENTS

Figure 1:
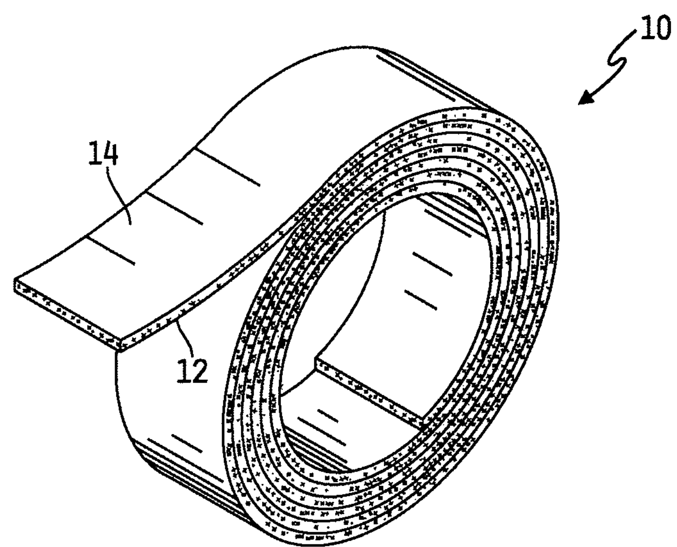
FIG. 1 is a perspective view of the wrap of this invention.

For the purposes of promoting an understanding of the principles of the invention, reference will now be made to a number of illustrative embodiments illustrated in the drawings and specific language will be used to describe the same. The preferred embodiment herein described is not intended to be exhaustive or to limit the invention to the precise form disclosed. It is chosen and described to explain the principles of the invention, and its application and practical use to enable others skilled in the art to utilize its teachings.

FIG. 1 illustrates the compression wrapping material 10 of this invention. Compression wrap 10 illustratively is formed of a foamed resinous material, preferably foamable PVC resin, which has incorporated thereinto a quantity of plasticizing agent which exceeds the amount of plasticizer normally needed to soften the material. The composition and manufacturing procedure for the foam is disclosed in U.S. Pat. No. 4,806,404, which is incorporated herein by reference. As stated in the example in column 2 of U.S. Pat. No. 4,806,404

EXAMPLE

The following compounds were mixed together: 100.0 parts of a foamable polyvinyl chloride resin (PVC), 140.0 parts of a phthalate plasticizer, 14.4 parts of a blowing agent plasticizer mix, 1.5 parts of an activator stabilizer and 1.0 parts of a cell stabilizer. A uniform mixture was cast at a height of 0.025 inch on conventional adhesive release paper, and chemically expanded by heating to approximately 385° F. Acrylic adhesive was applied to a closed cell polyethylene foam and allowed to dry. The PVC-plasticizer foam was then laminated to the polyethylene foam by passing through nip rollers.

Compression wrap 10 as shown is formed into a thin, elongated compression strip 12 of the foamed material and illustratively may, but need not be cast onto a smooth, glossy surface release paper 14 at between about 1/64 inch in height to about ½ inch in height. Illustratively, the compression wrap 10 need not have the release paper 14. The width of strip 12 is normally between about ½ inch to about 6 inches depending upon intended use, and can be formed in various lengths up to at least about 1000 feet. The width can be less than about ½ inch and can exceed about 6 inches including widths in excess of about fifty-six inches. Compression strip 12 may, but need not be wound on a dispensing roll 16 (not shown) with the release paper 14 separating overlapping rolls of the strip to prevent premature adhesion. As noted, the release paper may be omitted whether or not a dispensing roll is used.

Figure 2:
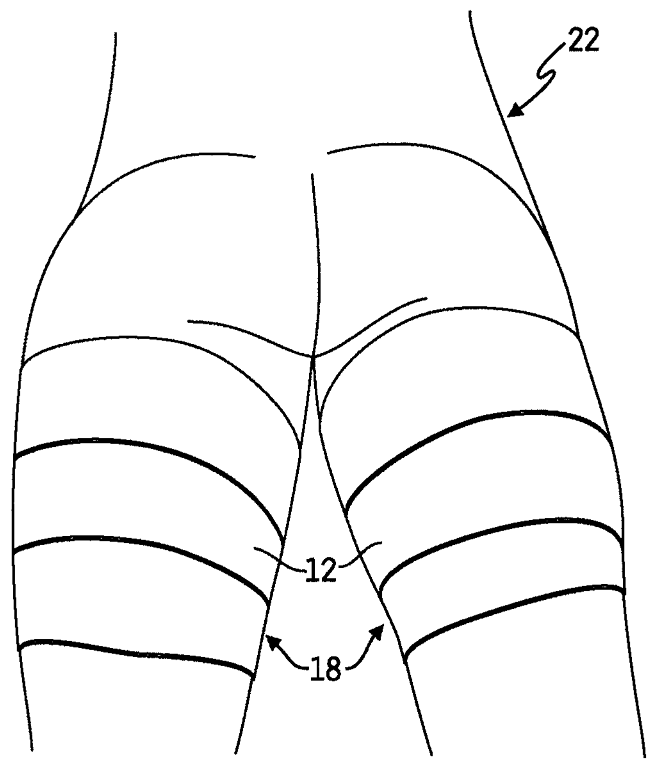
FIG. 2 is a perspective view of the wrap in use as a compression dressing on an animal after liposuction.
Figure 3:
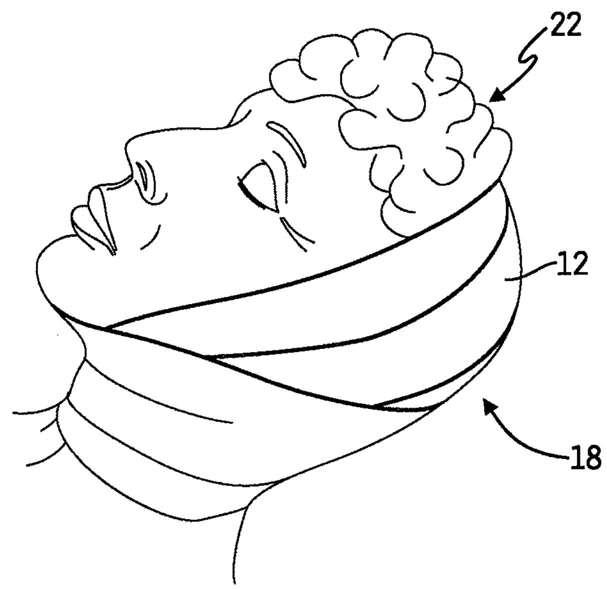
FIG. 3 is a perspective view of the wrap in use as a compression dressing on an animal after breast surgery.
Figure 4:
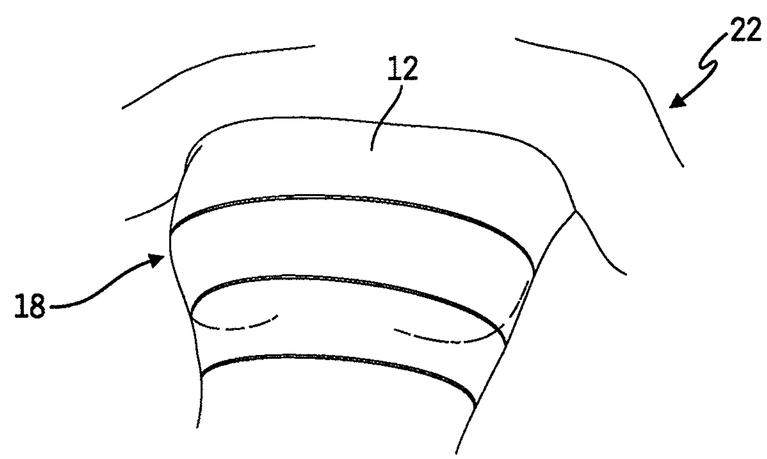
FIG. 4 is a perspective view of the wrap in use as a compression dressing on an animal after face or neck surgery.

FIGS. 2-4 illustrate compression strip 12 in use in different illustrative applications: liposuction (FIG. 2), breast augmentation and/or reduction (FIG. 3) and face/neck lift (FIG. 4). Each such application illustratively may use different and selected wrapping techniques, tensions, pressures and the like at the discretion, selection or desire of the user, for example a doctor, and the contour and/or size of the body part to be wrapped. It will be appreciated that the patient need not be a human, but could be any animal as desired.

To apply the illustrative compression wrappings or bandages 18 to a body part of an animal 22, illustratively in FIGS. 2-4 a human being, a user finds a string point and unrolls the compression strip 12 off of its dispensing roll, if it has one, or off of itself 12 if it does not have a dispensing roll to wrap the strip in an illustrative spiral wound overlap fashion. Different forms and methods of overlaps as best determined by the user according to the surgical or other procedure performed on the animal as known to those skilled in the art fall within the scope of the invention. Compression wrap or strip 12 so applied provides compression to for example a surgery site and also promotes healing of for example suture sites due to the air permeable nature of the foam. When the bandage 18 gets dirty, or when the compression pressure is desired to be changed, the wrapping or bandage 18 may be removed, washed and reapplied quickly as desired. Illustratively, the compression strip 12 may be applied to maintain a selected pressure that is uniform throughout the surface of the animal, or may be applied to apply different and varied selected pressures at different points on the surface of the animal. The compression strip may also be applied to maintain or conform to a selected contour of the surface as desired. So too, the tension, pressure, contour and/or manner of wrapping may be altered quickly and selectively.

While the invention has been illustrated and described in detail in the foregoing drawings and description, the same is to be considered as illustrative and not restrictive in character, it being understood that only illustrative embodiments thereof have been shown and described and that all changes and modifications that come within the spirit of the invention are desired to be protected.

What is claimed is:

1. A compression dressing for the surface of an animal comprising:

a compression wrap having a substantially uniform composition for forming the compression dressing in contact with the surface of the animal;

the compression wrap being in the form of a closed cell, self-adherent elongated strip formed of a vinyl foam which has had excess plasticizer cast into its mixture, the mixture forming a substantially uniform composition.

2. The compression dressing of claim 1 wherein the strip comprises a foamed material including a polymer and at least 40 weight percent of the foamed material is a plasticizer.

3. The compression dressing of claim 2 wherein the strip is applied to the surface in a spiral wound overlap fashion, without the use of a separate adhesive, so that the strip contacts and adheres to itself and the surface to form the compression dressing in contact with the surface of the animal.

4. The compression dressing of claim 3 wherein the compression dressing applies a selected pressure to the surface.

5. The compression dressing of claim 4 wherein the strip retains generally constant the selected pressure until altered by a user.

6. The compression dressing of claim 3 wherein the strip conforms to a contour of the surface.

7. The compression dressing of claim 6 wherein the strip retains the contour until altered by a user.

8. The compression dressing of claim 3 wherein the strip is washable and reusable to form the compression dressing without loss of its self-adherent characteristic.

9. The compression dressing of claim 3 wherein the strip may be applied in a manner to apply selected and varied pressures at different locations on the surface as desired, the compression dressing maintaining generally constant the varied pressures at the different locations on the surface.

10. The compression dressing of claim 3 wherein the compression dressing comprises a bandage.

11. A method of applying compression to a surface of an animal, the method comprising the steps of:

applying to the surface of an animal a closed cell compression wrap having a substantially uniform composition in a spiral wound overlap fashion, without the use of a separate adhesive, so that the wrap contacts and adheres to itself and the surface to form a compression dressing in contact with the surface of the animal, the closed cell compression wrap consisting essentially of a vinyl foam which has had excess plasticizer cast into its mixture, the mixture forming a substantially uniform composition.

12. The method of applying compression to a surface of an animal according to claim 11 wherein the compression wrap comprises a foamed material including a polymer and at least 40 weight percent of the foamed material is a plasticizer.

13. The method of applying compression to a surface of an animal according to claim 12 wherein the compression wrap is washable and reusable to form the compression dressing without loss of its self-adherent characteristic.

14. The compression dressing of claim 12 wherein the compression dressing comprises a bandage.

15. The method of applying compression to a surface of an animal according to claim 11 further comprising the step of applying the compression wrap to apply a selected pressure to the surface.

16. The method of applying compression to a surface of an animal according to claim 15 wherein the compression wrap maintains generally constant the selected pressure until altered by a user.

17. The method of applying compression to a surface of an animal according to claim 15 further comprising the step of applying the compression wrap to vary the selected pressure at different locations on the surface as desired.

18. The method of applying compression to a surface of an animal according to claim 11 further comprising the step of applying the compression wrap to conform to a contour of the surface.

19. The method of applying compression to a surface of an animal according to claim 18 wherein the wrap retains the desired contour until altered by a user.

20. A method of applying compression to a surface of an animal, the method comprising the steps of:

wrapping in a spiral wound overlap fashion around the surface of the animal a closed cell compression dressing having a substantially uniform composition; the compression dressing comprising a self-adherent elongated strip formed of a vinyl foam which has had excess plasticizer cast into its mixture, the mixture forming a substantially uniform composition; and maintaining a selected pressure at the surface of the animal.

21. A compression dressing for wrapping the surface of an animal, the compression dressing being composed of an elongated strip of a self-adherent single-layer material, the single-layer material having a substantially uniform composition comprising a closed cell vinyl foam which has had excess plasticizer cast into its mixture, the mixture forming a substantially uniform composition.

22. A compression dressing for the surface of an animal comprising:

compression wrap having a substantially uniform composition for forming the compression dressing in contact with the surface of the animal;

the compression wrap being in the form of a closed cell, self-adherent elongated strip formed of a polyurethane foam which has had excess plasticizer cast into its mixture, the mixture forming a substantially uniform composition.

* * * * *